United States Patent
Ando (10) Patent No.: US 10,314,466 B2
(45) Date of Patent: Jun. 11, 2019

(54) CONDUIT CONTROL DEVICE

(71) Applicant: OLYMPUS CORPORATION, Tokyo (JP)

(72) Inventor: Atsushi Ando, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/633,813

(22) Filed: Jun. 27, 2017

(65) Prior Publication Data

US 2017/0290495 A1   Oct. 12, 2017

Related U.S. Application Data (63) Continuation of application No. PCT/JP2016/080315, filed on Oct. 13, 2016.

(30) Foreign Application Priority Data

Feb. 29, 2016 (JP) ................... 2016-037582

(51) Int. Cl.
*A61B 1/00* (2006.01)
*A61B 1/12* (2006.01)
*A61B 1/015* (2006.01)
*A61M 39/22* (2006.01)

(52) U.S. Cl.
CPC .......... *A61B 1/015* (2013.01); *A61B 1/00068* (2013.01); *A61B 1/12* (2013.01); *A61M 39/22* (2013.01)

(58) Field of Classification Search
CPC ....... A61B 1/00068; A61B 1/015; A61B 1/12; A61B 1/00137; A61M 39/22; A61M 39/20
See application file for complete search history.

(56) References Cited

U.S. PATENT DOCUMENTS

| | | | | | |
|---|---|---|---|---|---|
| 4,736,732 | A | * | 4/1988 | Shimonaka | A61M 1/0043 600/158 |
| 4,800,869 | A | * | 1/1989 | Nakajima | A61B 1/00068 600/158 |
| 4,860,731 | A | * | 8/1989 | Matsuura | A61B 1/00068 600/157 |
| 5,301,656 | A | * | 4/1994 | Negoro | A61B 1/0052 600/133 |
| 5,840,015 | A | * | 11/1998 | Ogino | A61B 1/00068 600/159 |

(Continued)

FOREIGN PATENT DOCUMENTS

CN 202376065 U 8/2012
CN 104853667 A 8/2015

(Continued)

*Primary Examiner* — Aaron B Fairchild
(74) *Attorney, Agent, or Firm* — Scully, Scott, Murphy & Presser, P.C.

(57) ABSTRACT

A conduit control device includes a cylinder member, a piston member, an attachment section including a rigid cylinder, a compression spring, a first elastic member being brought into contact with a contact surface of the rigid cylinder and elastically deformed to thereby seal a gap in a state in which the piston member is depressed via the button section, and a second elastic member brought into contact with an exterior member and elastically deformed to thereby seal a gap in a state in which the piston member is depressed via the button section.

8 Claims, 12 Drawing Sheets

(56) References Cited

U.S. PATENT DOCUMENTS

| | | |
|---|---|---|
| 2012/0088973 A1 | 4/2012 | Morimoto |
| 2015/0011831 A1* | 1/2015 | Ouchi ................ A61B 1/00068 |
| | | 600/159 |
| 2015/0257634 A1 | 9/2015 | Nakade |

FOREIGN PATENT DOCUMENTS

| | | |
|---|---|---|
| JP | S62-106739 A | 5/1987 |
| JP | S62-189041 A | 8/1987 |
| JP | 2000-000206 A | 1/2000 |
| JP | 2001-157663 A | 6/2001 |
| JP | 2009-000300 A | 1/2009 |
| JP | 4583915 B2 | 11/2010 |
| JP | 2013-066666 A | 4/2013 |
| JP | 2013-202099 A | 10/2013 |

* cited by examiner

CONDUIT CONTROL DEVICE

CROSS REFERENCE TO RELATED APPLICATION

This application is a continuation application of PCT/JP2016/080315 filed on Oct. 13, 2016 and claims benefit of Japanese Application No. 2016-037582 filed in Japan on Feb. 29, 2016, the entire contents of which are incorporated herein by this reference.

BACKGROUND OF INVENTION

1. Field of the Invention

The present invention relates to a conduit control device that is provided in an operation section of an endoscope and switches a communication state of a conduit provided inside the endoscope.

2. Description of the Related Art

An endoscope makes it possible to observe, by inserting an elongated insertion section into a subject, an inside of the subject using an observation lens provided at a distal end of the insertion section.

A configuration is also well known in which an opening of a suction conduit is provided at the distal end of the insertion section. The suction conduit is a conduit for sucking at least one of a solid and a fluid inside the subject via the opening.

The suction conduit is inserted through the insertion section of the endoscope, an operation section consecutively connected to a proximal end of the insertion section, a universal cord extended from the operation section, and a connector provided at an extension end of the universal cord. The suction conduit is connected to, via the connector, a suction pump provided outside the endoscope.

A configuration is also well known in which a conduit control device is provided in the operation section of the endoscope. The conduit control device switches, for example, suction of at least one of the solid and the fluid from the opening of the suction conduit to a suction state and a cutoff state.

More specifically, the conduit control device includes a cylinder member provided in a halfway position of the suction conduit, a piston member slidable into the cylinder member, and a compression spring that urges the piston member in a direction in which the piston member projects from an opening of the cylinder member.

That is, an upstream side and a downstream side of the suction conduit are respectively connected to the cylinder member. The conduit control device switches a communication state of the upstream side and the downstream side of the suction conduit between communication and cutoff.

As an example of a configuration of the conduit control device, a main part of the piston member includes a shaft section slidable into the cylinder member and a button section provided at a top of the shaft section. Note that a communication path for causing the upstream side and the downstream side of the suction conduit to communicate with each other is formed in the shaft section.

On one hand, in a state in which the button section is not operated by an operator, the piston member is located with a part of the piston member projected from the opening of the cylinder member by the compression spring. An outer circumferential surface of the shaft section closes a downstream side opening of the suction conduit in the cylinder member. Consequently, the communication between the upstream side and the downstream side of the suction conduit is cut off.

On the other hand, in a state in which the button section is depressed by the operator, the compression spring is compressed and the shaft section is depressed inside the cylinder member. A state in which the downstream side opening of the suction conduit is closed by the outer circumferential surface of the shaft section is released by a shaft section through-hole that is opened on the outer circumferential surface of the shaft section and communicates with the communication path. Therefore, the upstream side and the downstream side of the suction conduit communicate with each other via the communication path and the shaft section through-hole.

With the configuration described above, the conduit control device switches the communication state of the upstream side and the downstream side of the suction conduit between the communication and the cutoff.

Japanese Patent No. 4583915 discloses a configuration of a conduit control device provided with an attachment section that enables a piston member to be attached to and detached from a cylinder member such that the piston member can be detached from the cylinder member in order to improve a cleaning/disinfecting property inside the cylinder member.

The attachment section includes a through-hole through which a shaft section of the piston member is inserted and a claw section made of resin capable of being engaged with and disengaged from a pipe sleeve provided near an opening of the cylinder member. Therefore, the attachment section has a function of deforming the claw section and detaching the claw section from the pipe sleeve to thereby detach the piston member from the cylinder member.

Further, Japanese Patent No. 4583915 also discloses a structure in which the shaft section of the piston member is made of resin in order to reduce manufacturing cost.

SUMMARY OF THE INVENTION

A conduit control device according to an aspect of the present invention is a conduit control device of an endoscope that is provided inside an operation section of the endoscope and switches a communication state of a conduit provided in the endoscope. The conduit control device includes: a cylinder member; a piston member, a shaft section of which is provided to be slidable into the cylinder member, the piston member including a button section at a top of the shaft section; an attachment section including a rigid cylinder detachably attachable to a vicinity of an opening of the cylinder member in an exterior of the operation section and including a through-hole through which the shaft section is inserted and an elastic cylinder integrally formed on an outer circumferential surface of the rigid cylinder; a compression spring suspended between the button section and the rigid cylinder, the compression spring urging the piston member with respect to the rigid cylinder in a direction in which the button section projects from the opening; a first elastic member provided on the projecting direction side with respect to a position at which one end of the compression spring comes into contact in the button section, the first elastic member being brought into contact with a contact surface, which is provided on an inner circumferential surface of the rigid cylinder, and elastically deformed to thereby seal a gap between the attachment section and the piston member in a state in which the piston member is depressed via the button section; and a second elastic member provided in a position of the elastic cylinder in contact with the exterior of the operation section, the second elastic member being brought into contact with the exterior and elastically deformed to thereby seal a gap between the attachment section and the exterior in a state in which the piston member is depressed via the button section.

DETAILED DESCRIPTION OF THE PREFERRED EMBODIMENT(S)

An embodiment of the present invention is described below with reference to the drawings. Note that the drawings are schematic and relations between thicknesses and widths of respective members, ratios of the thicknesses of the respective members, and the like are different from real ones. It goes without saying that portions, relations and ratios of dimensions of which are different from one another, are included among the drawings.

Figure 1:
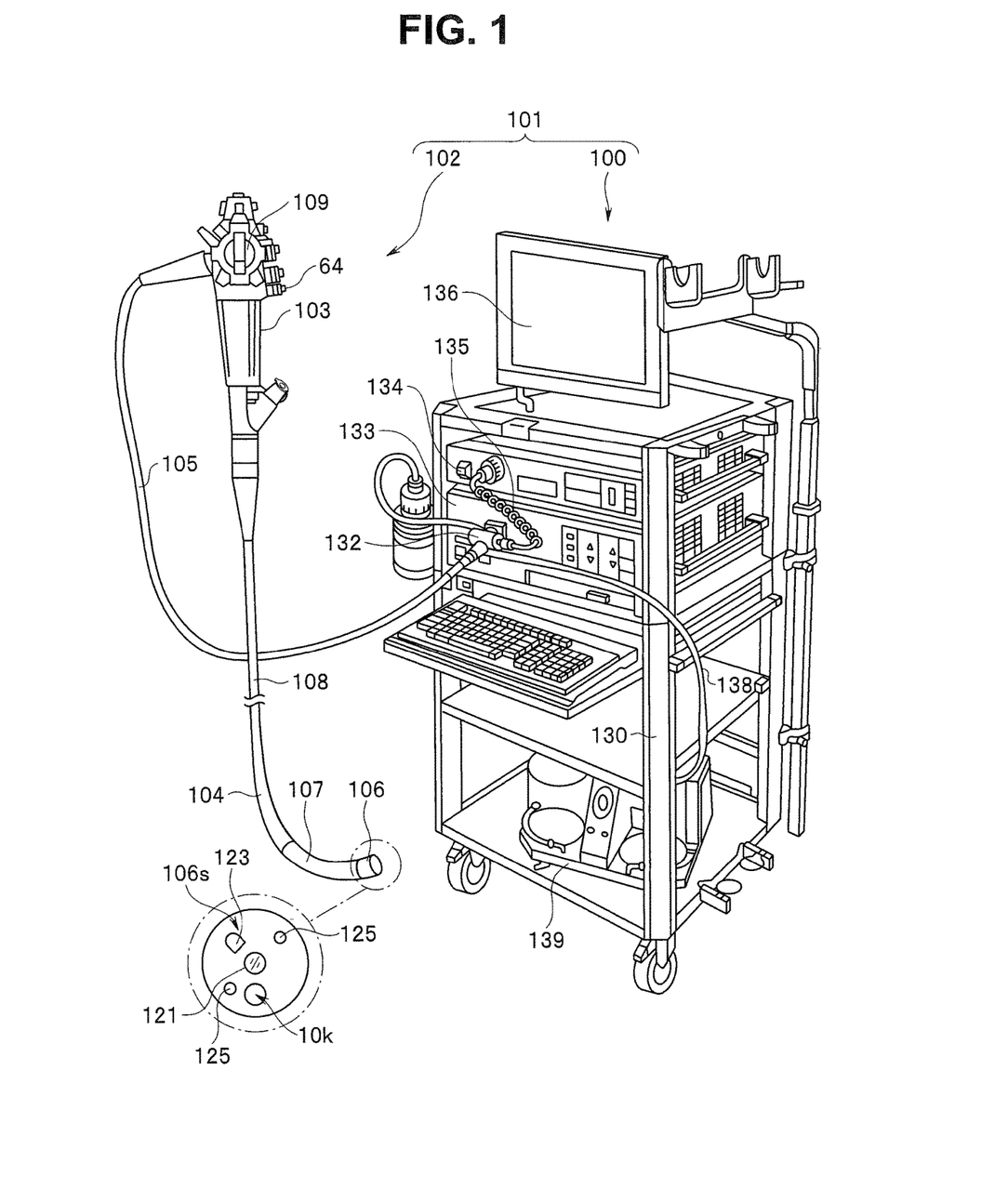
FIG. 1 is a diagram schematically showing an endoscope apparatus including an endoscope in which a conduit control device according to an embodiment is provided.

FIG. 1 is a diagram schematically showing an endoscope apparatus including an endoscope in which a conduit control device according to the present embodiment is provided.

Figure 2:
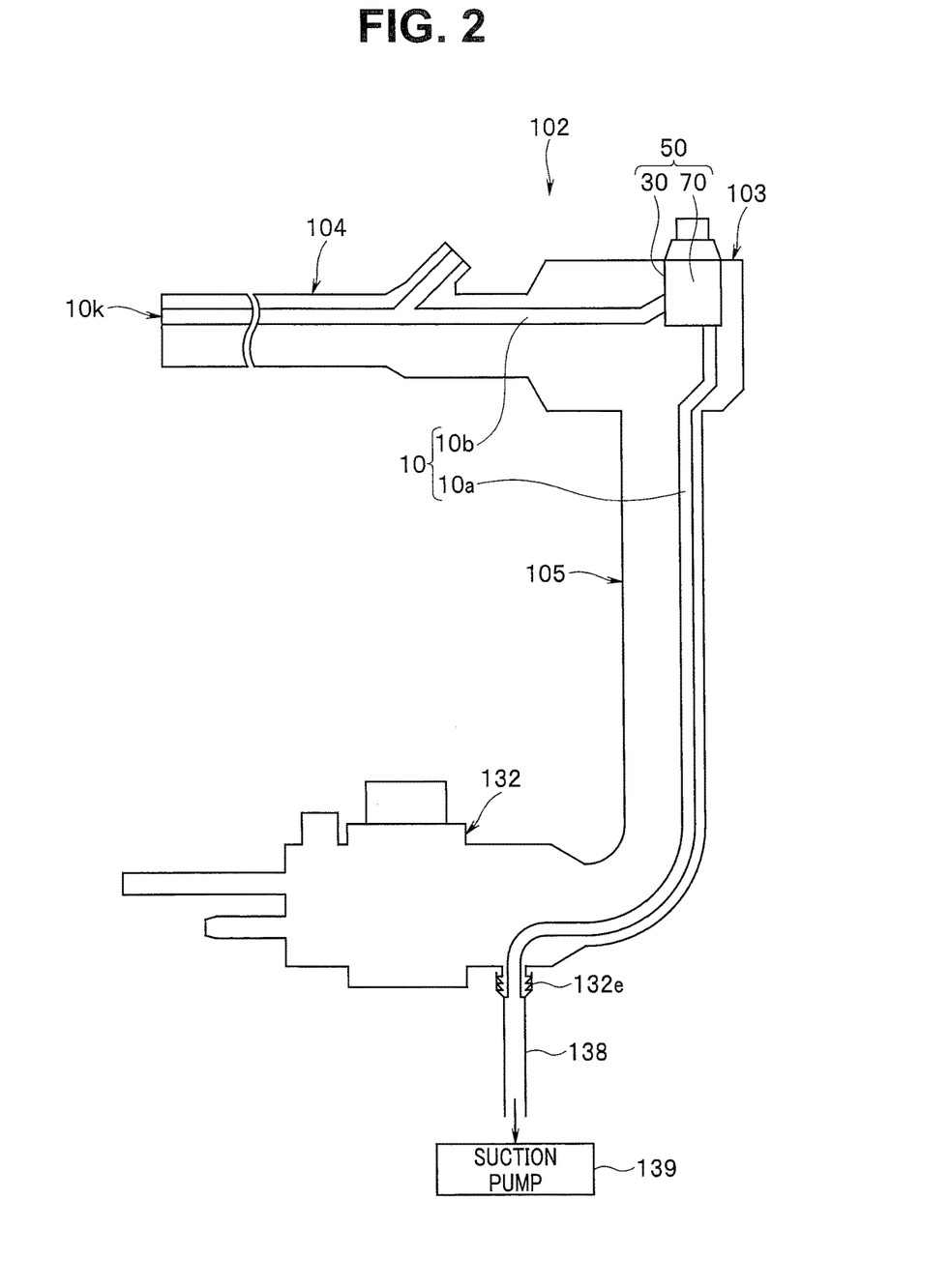
FIG. 2 is a diagram schematically showing, together with a suction pump, a configuration of a suction conduit in the endoscope shown in FIG. 1.

FIG. 2 is a diagram schematically showing, together with a suction pump, a configuration of a suction conduit in the endoscope shown in FIG. 1.

As shown in FIG. 1, a main part of an endoscope apparatus 101 includes an endoscope 102 and a peripheral apparatus 100.

The peripheral apparatus 100 includes a light source apparatus 133, a video processor 134, a monitor 136, and a suction pump 139, each placed on a stand 130.

A main part of the endoscope 102 includes an insertion section 104 inserted into a subject, an operation section 103 consecutively connected to a proximal end of the insertion section 104, a universal cord 105 extended from the operation section 103, and a connector 132 provided at an extension end of the universal cord 105. The connector 132 is detachably attachable to the light source apparatus 133.

Note that the connector 132 and the video processor 134 are electrically connected by a connection cable 135. A tube 138 extended from the suction pump 139 is connected to a suction pipe sleeve 132e (see FIG. 2) of the connector 132.

The insertion section 104 is configured by a distal end portion 106 located on a distal end side of the insertion section 104, a bending section 107 bent in, for example, upper, lower, left, and right four directions by a bending operation knob 109 provided in the operation section 103, and a flexible tube section 108 consecutively connected to a proximal end of the bending section 107.

On a distal end face 106s of the distal end portion 106, an opening 10k of a suction conduit 10 provided in the endoscope 102, an observation lens 121, an air/water feeding nozzle 123, an illumination window 125, and the like are provided.

A not-shown air/water feeding button provided in the operation section 103 is operated, whereby the air/water feeding nozzle 123 supplies liquid to the observation lens 121 to thereby remove stains adhering to the observation lens 121.

Further, the air/water feeding nozzle 123 supplies gas into the subject to expand an inside of the subject and secure an observation visual field of the observation lens 121.

The illumination window 125 supplies illumination light into the subject. Note that, instead of the illumination window 125, a light emitting element such as an LED may be provided on the distal end face 106s.

The suction conduit 10 is used when at least one of a solid and a fluid inside the subject is sucked via the opening 10k.

The suction conduit 10 includes a downstream-side suction conduit (hereinafter simply referred to as suction conduit) 10b provided inside the insertion section 104 and the operation section 103 and having the opening 10k and an upstream-side suction conduit (hereinafter simply referred to as suction conduit) 10a provided inside the operation section 103, the universal cord 105, and the connector 132 and connected to the suction pipe sleeve 132e.

The suction conduits 10a and 10b are connected to a cylinder member 30 of a conduit control device 50 that switches a communication state of the suction conduit 10 provided in the operation section 103.

On one hand, in a non-operation state of a suction button 64, which is a button section of the conduit control device 50, provided in the operation section 103, the suction pump 139 sucks in air outside of the endoscope 102 via the tube 138, the suction conduit 10a, and the conduit control device 50.

On the other hand, in a state in which the suction button 64 is depressed by the operator, the suction pump 139 sucks at least one of the solid and the fluid inside the subject via the tube 138, the suction conduit 10a, the conduit control device 50, the suction conduit 10b, and the opening 10k.

Note that the suction pump 139 is always driven after power-on irrespective of whether the suction button 64 is depressed by the operator.

A main part of the conduit control device 50 includes the cylinder member 30, a piston unit 70 retractably fit and inserted into the cylinder member 30, and a compression spring 80.

The conduit control device 50 switches a communication state of the suction conduit 10a and the suction conduit 10b to communication and cutoff.

Figure 3:
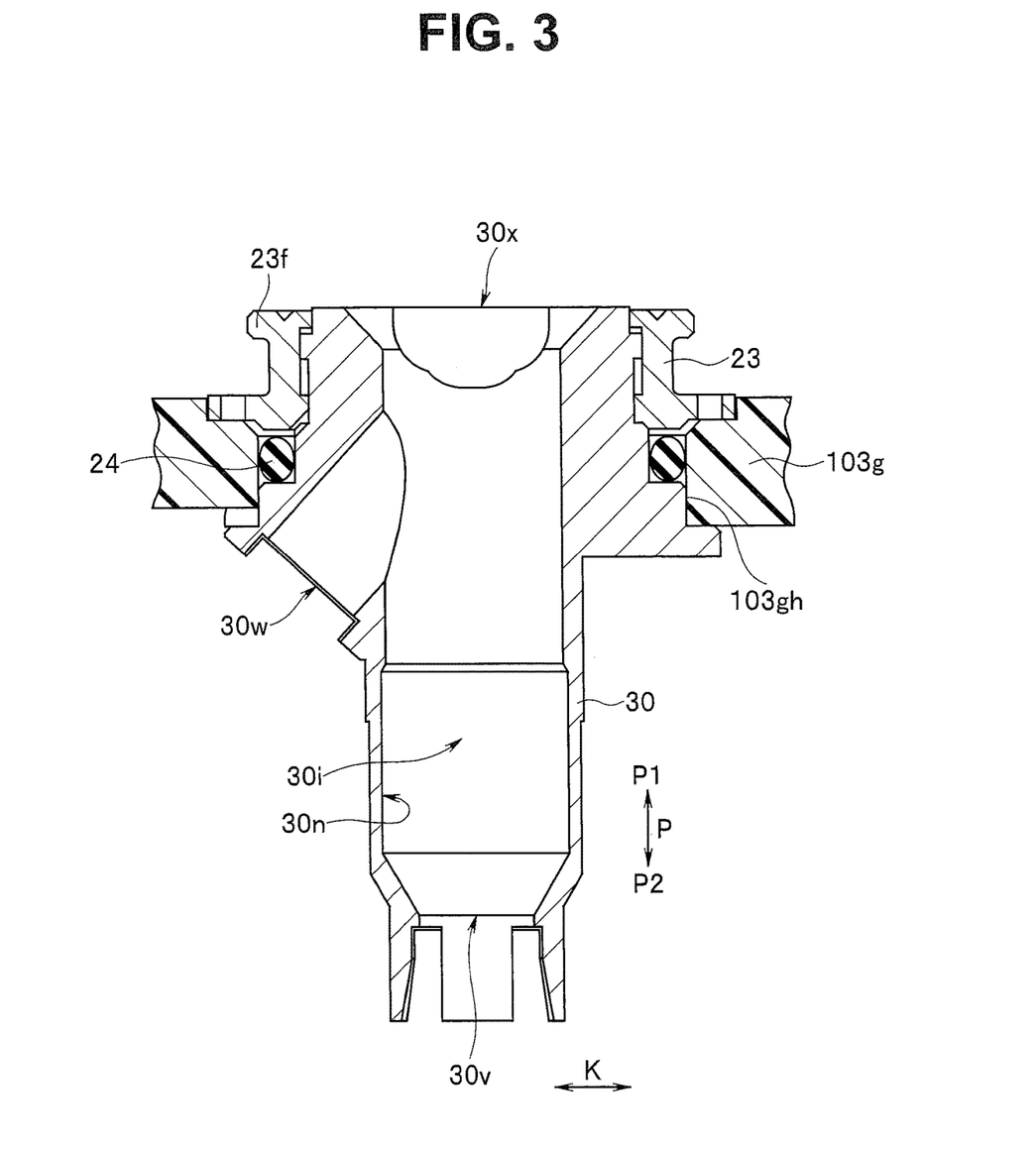
FIG. 3 is a partial sectional view showing, together with an exterior member of an operation section of the endoscope, a cylinder member of the conduit control device shown in FIG. 2.

A configuration of the conduit control device 50 shown in FIG. 2 is described with reference to FIG. 3 to FIG. 8. FIG. 3 is a partial sectional view showing, together with an exterior member of the operation section of the endoscope, the cylinder member of the conduit control device shown in FIG. 2.

Figure 4:
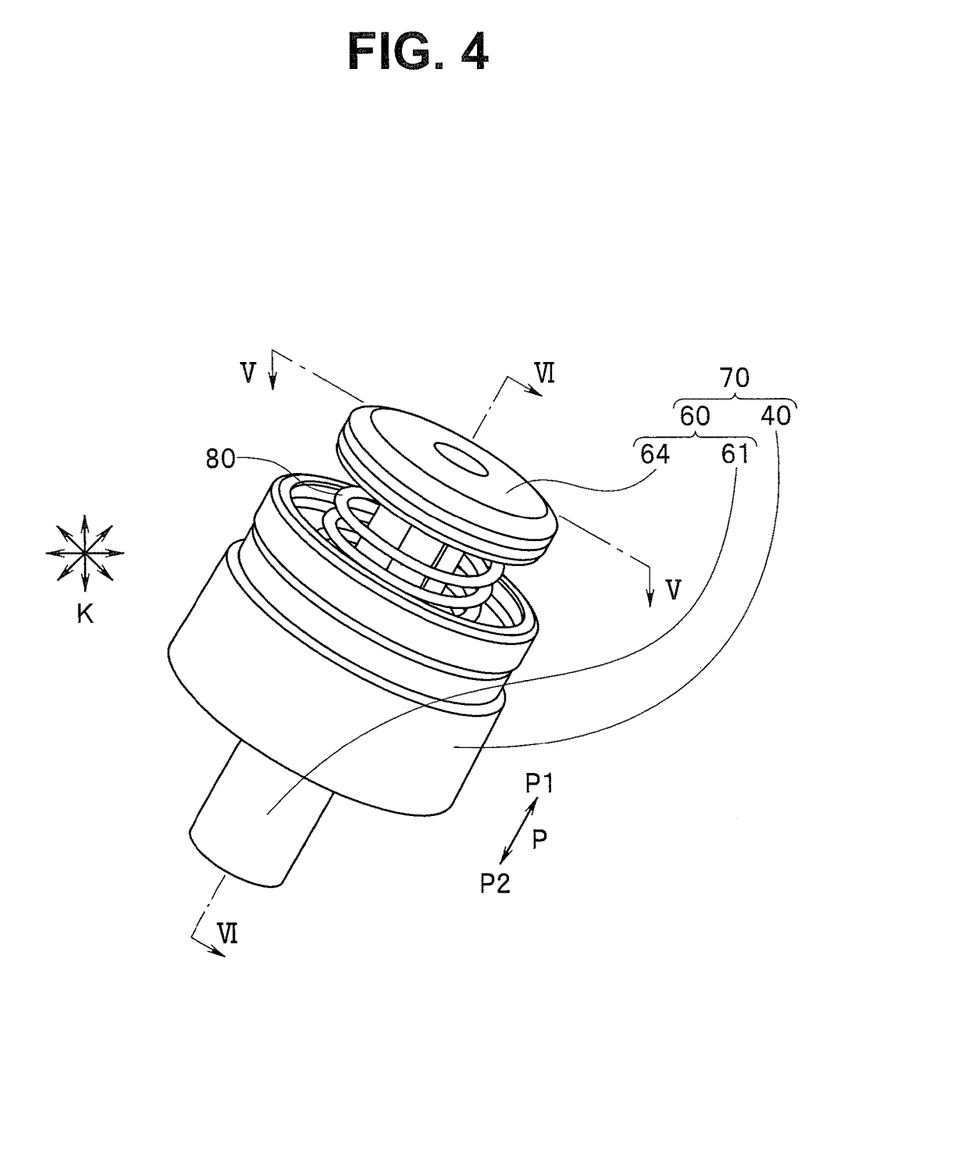
FIG. 4 is a perspective view showing a piston unit of the conduit control device shown in FIG. 3.
Figure 5:
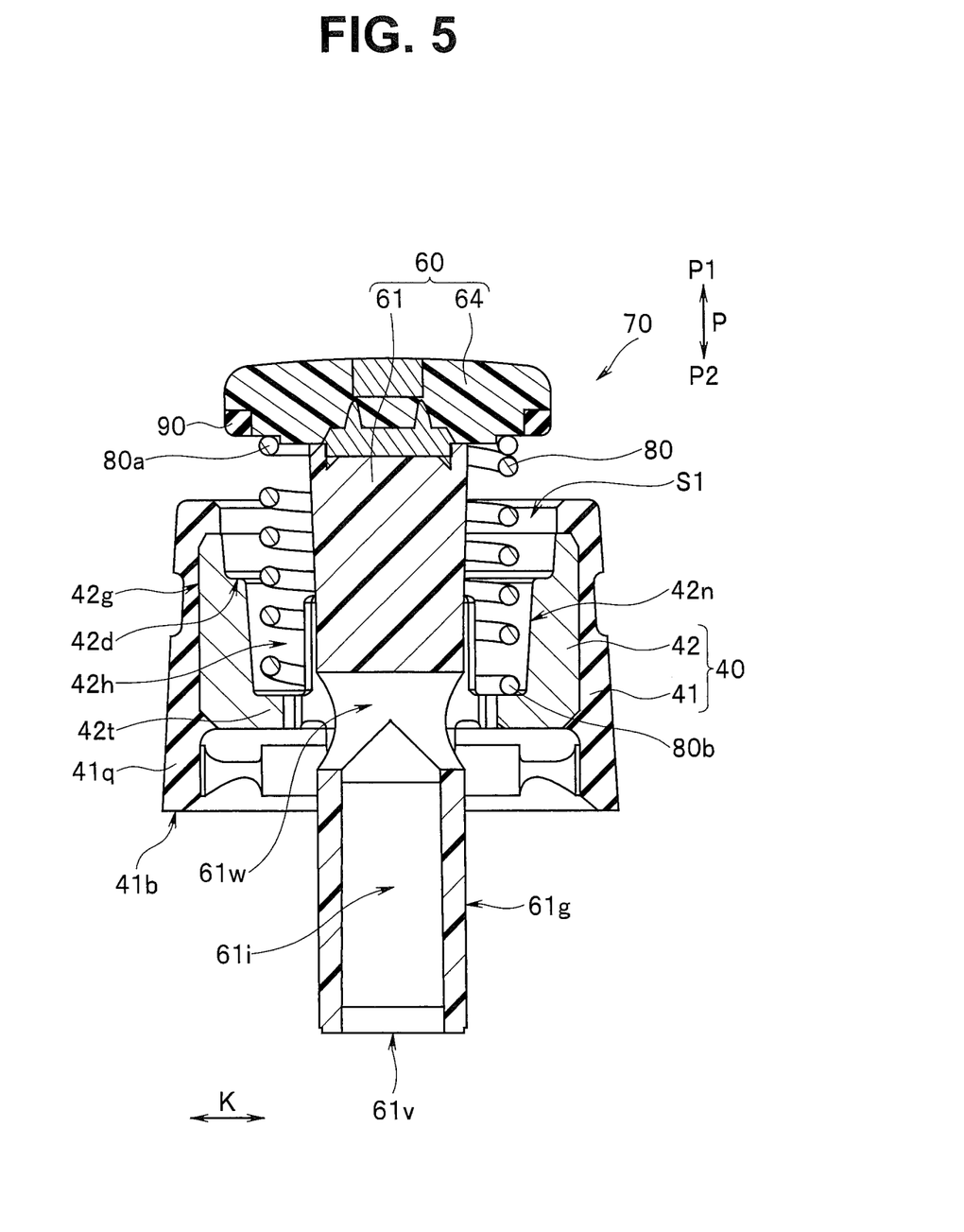
FIG. 5 is a sectional view of the piston unit along a V-V line in FIG. 4.
Figure 6:
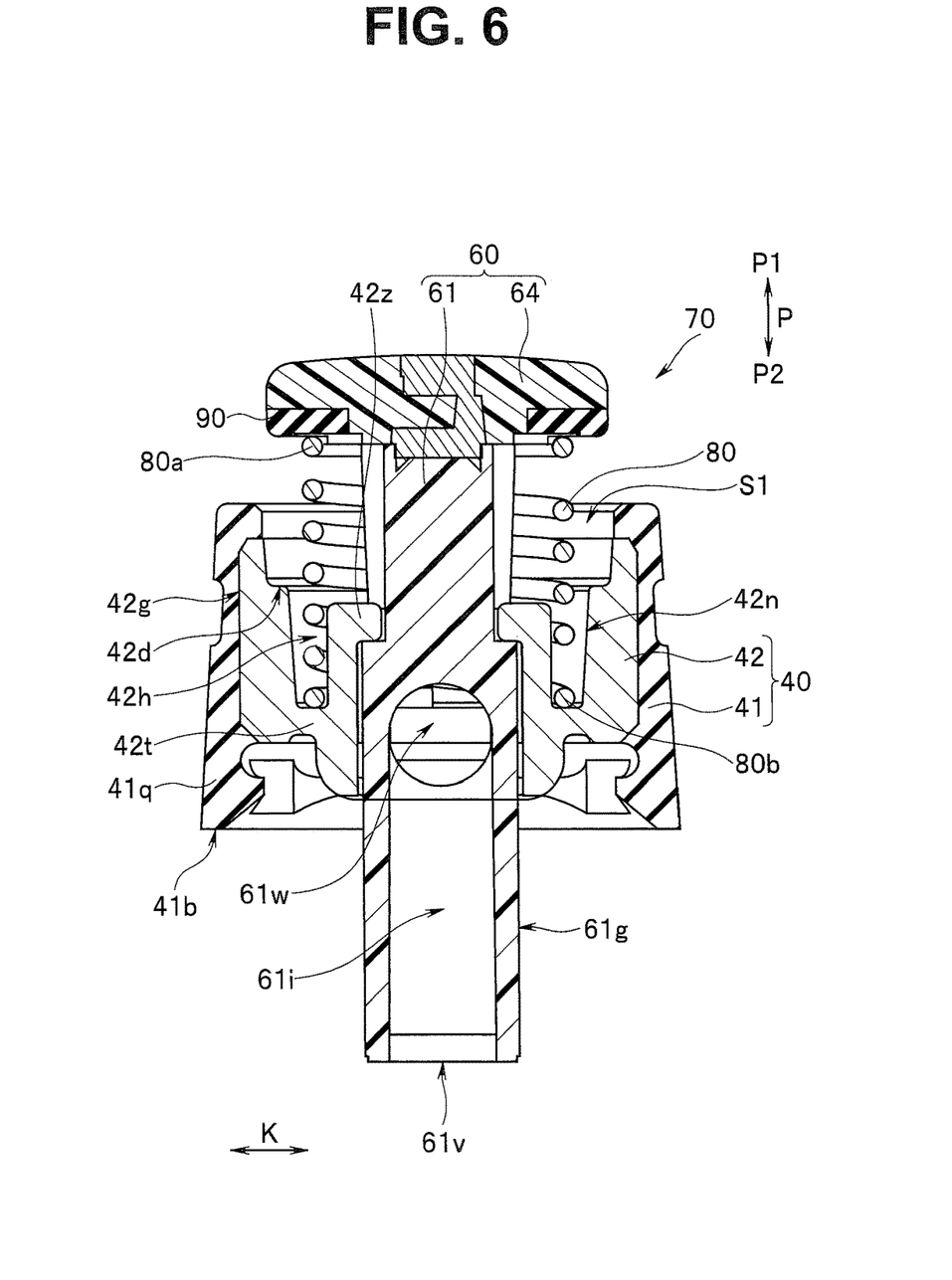
FIG. 6 is a sectional view of the piston unit along a VI-VI line in FIG. 4.

FIG. 4 is a perspective view showing the piston unit of the conduit control device shown in FIG. 3. FIG. 5 is a sectional view of the piston unit along a V-V line in FIG. 4. FIG. 6 is a sectional view of the piston unit along a VI-VI line in FIG. 4.

Figure 7:
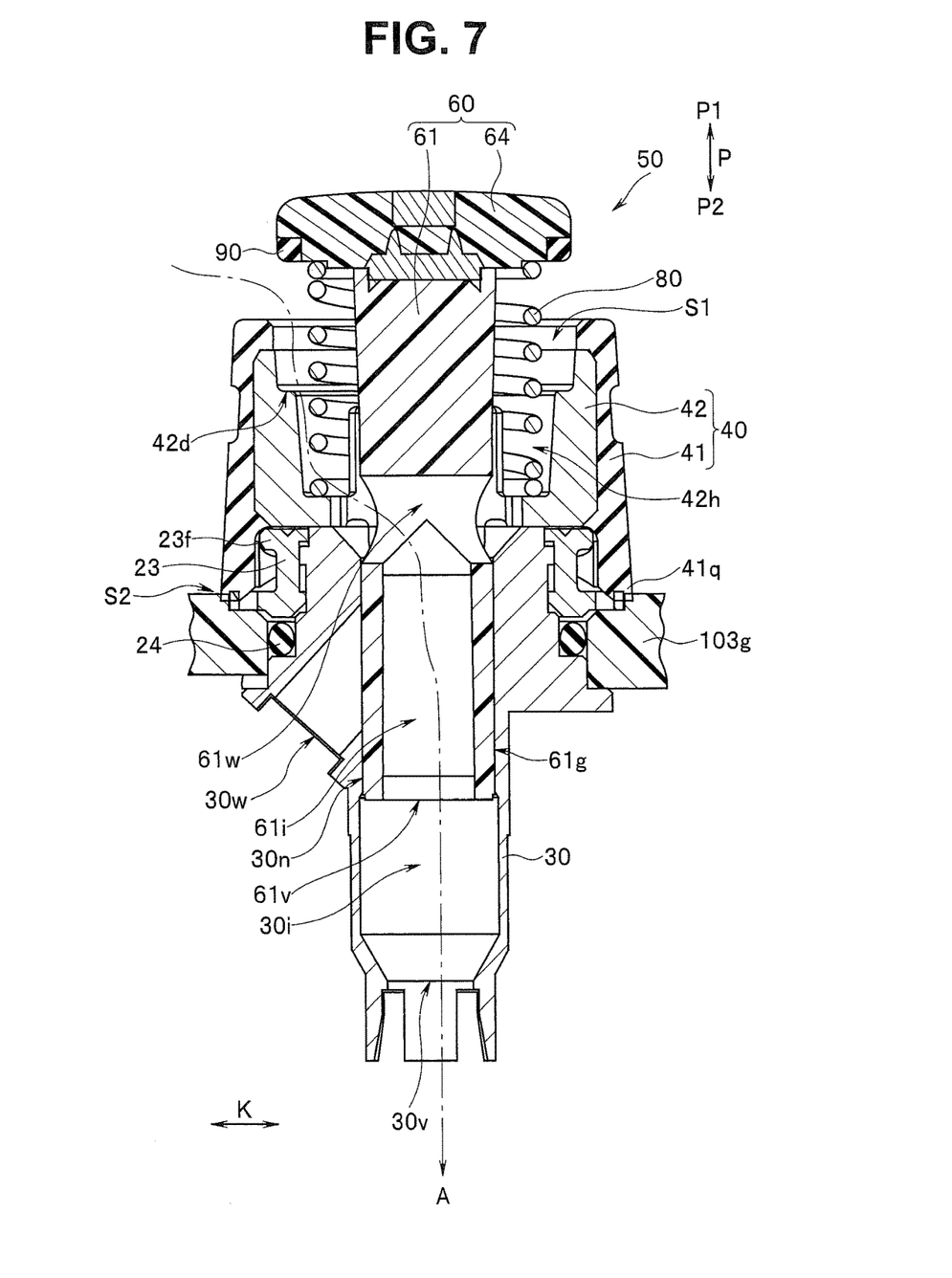
FIG. 7 is a partial sectional view showing a state in which the piston unit shown in FIG. 5 is mounted inside the cylinder member shown in FIG. 3.
Figure 8:
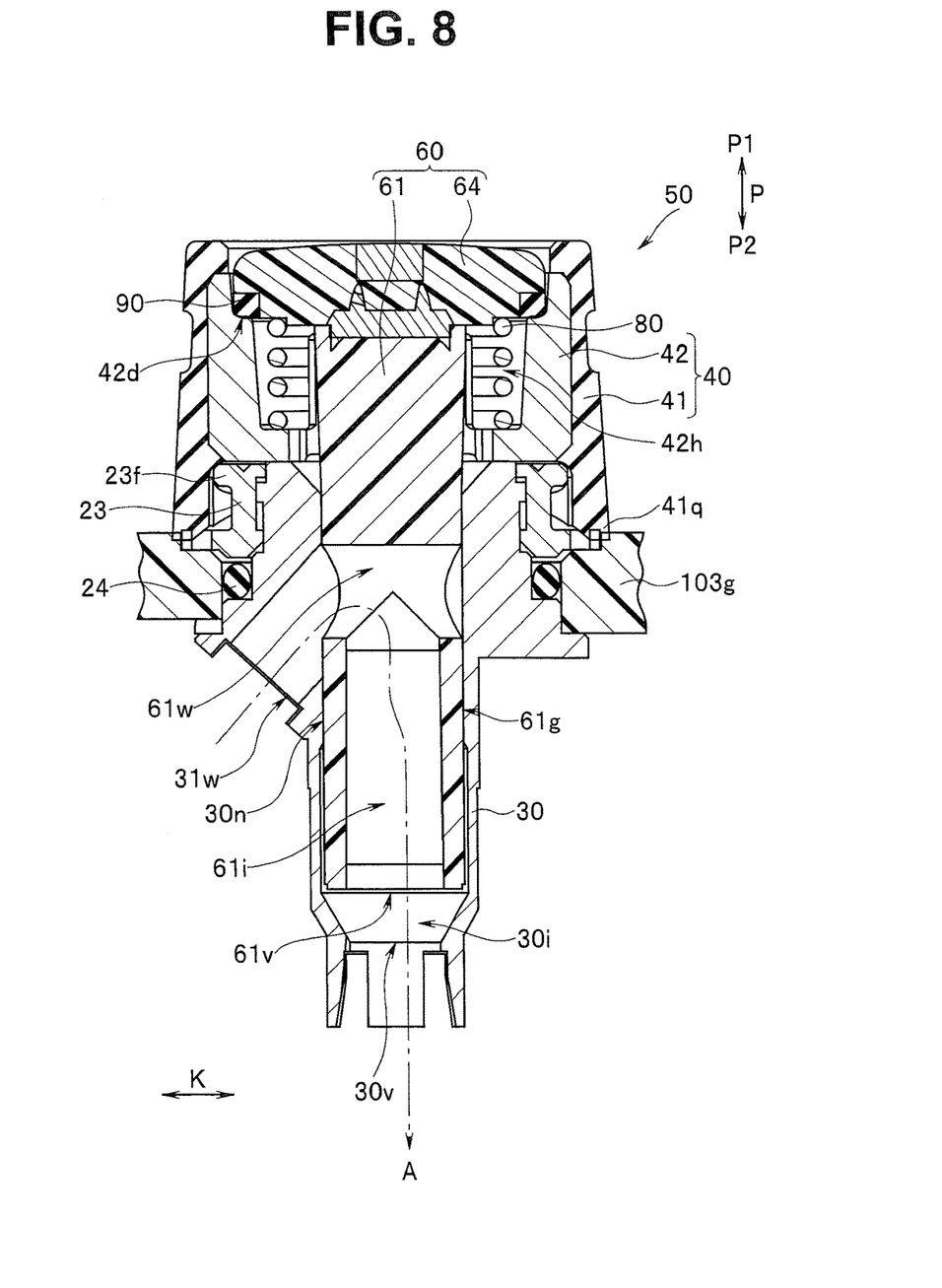
FIG. 8 is a partial sectional view showing a state in which a piston member of the piston unit shown in FIG. 7 is depressed and an upstream side and a downstream side of the suction conduit communicate with each other.

Further, FIG. 7 is a partial sectional view showing a state in which the piston unit shown in FIG. 5 is mounted inside the cylinder member shown in FIG. 3. FIG. 8 is a partial sectional view showing a state in which a button section of a piston member of the piston unit shown in FIG. 7 is depressed and the upstream side and the downstream side of the suction conduit communicate with each other.

As shown in FIG. 3, in an exterior member 103g configuring the operation section 103, an attachment hole 103gh is formed to pierce through the exterior member 103g in an extending direction P of the cylinder member 30.

The cylinder member 30 configured in a cylindrical shape from, for example, metal is water-tightly and air-tightly fixed to the attachment hole 103gh by a nut 23 via an O-shaped ring 24.

A first opening section 30w, to which the suction conduit 10b is connected, is formed in a sidewall of the cylinder member 30.

A second opening section 30v, to which the suction conduit 10a is connected, is formed at a lower end in the extending direction P (hereinafter simply referred to as lower end) of the cylinder member 30. Further, a third opening section 30x communicating with an outside of the operation section 103 is formed at an upper end in the extending direction P (hereinafter simply referred to as upper end) of the cylinder member 30.

Note that the first opening section 30w, the second opening section 30v, and the third opening section 30x communicate with one another through a piston insert through-hole 30i formed along the extending direction P in the cylinder member 30.

In the nut 23, a flange section 23f, to which a claw section 41q of an elastic cylinder 41 of an attachment section 40 described below in the piston unit 70 is locked, is formed.

A main part of the piston unit 70 includes, as shown in FIG. 4 to FIG. 6, a piston member 60 and the attachment section 40.

The piston member 60 is made of, for example, resin. The piston member 60 includes a shaft section 61 slidable along the extending direction P into the piston insert through-hole 30i via the third opening section 30x of the cylinder member 30 and the suction button 64 fixed to, for example, by screwing and bonding, a top in a direction (hereinafter referred to as upward direction) P1 in which the shaft section 61 projects from the third opening section 30x in the extending direction P.

A communication path 61i is formed along the extending direction P on an inside of the shaft section 61. An opening 61v of the communication path 61i is formed at a lower end of the shaft section 61. A through-hole 61w piercing through the shaft section 61 in a radial direction K and communicating with a communication path 61i is formed in a halfway position in the extending direction P of the shaft section 61.

As described above, when suction of at least one of the solid and the fluid in the subject is performed via the suction conduit 10, the suction button 64 is depressed by the operator. One end 80a of the compression spring 80 is in contact with the suction button 64. Note that, as shown in FIG. 8, the suction button 64 enters an inside of the attachment section 40 when the suction button 64 is depressed.

In the suction button 64, a first elastic member 90 is provided on an upper side and an outer side in the radial direction K with respect to a position at which the one end 80a of the compression spring 80 is in contact.

Since the first elastic member 90 is provided in the suction button 64 on the upper side and the outer side in the radial direction K with respect to the position at which the one end 80a of the compression spring 80 is in contact, a situation is prevented in which a position of the one end 80a shifts irrespective of depressing operation of the suction button 64 and the first elastic member 90 is scratched by the one end 80a. Note that a function of the first elastic member 90 is described below.

As a material configuring the first elastic member 90, a material having self-adhesiveness to the suction button 64 is desirable.

For example, when the suction button 64 is made of polycarbonate, the first elastic member 90 is desirably made of polyester-based elastomer resin.

When the suction button 64 is made of polypropylene, the first elastic member 90 is desirably made of a styrene-base thermoplastic elastomer resin.

Further, it has been known as a result of an experiment that, when the suction button 64 is made of polysulfone, the first elastic member 90 is desirably made of silicon.

Consequently, since an adhesive does not have to be used for formation of the first elastic member 90 on the suction button 64, it is possible to reduce molding cost and machining cost of the piston member 60.

Note that, a material configuring the first elastic member 90 is not limited to the materials described above and may be any material as long as the material has self-adhesiveness to the suction button 64 and has elasticity.

The attachment section 40 is detachably attachable to a vicinity of the third opening section 30x of the cylinder member 30 to thereby enable the piston unit 70 to be attached to and detached from the cylinder member 30.

The attachment section 40 includes a rigid cylinder 42 including a through-hole 42h extending along the extending direction P, through which the shaft section 61 is inserted, and an elastic cylinder 41 formed integrally with an outer circumferential surface 42g of the rigid cylinder 42.

The rigid cylinder 42 is made of, for example, metal. An inward projecting part 42t projecting to an inner side in the radial direction K is formed on an inner circumferential surface 42n at a lower end. A contact surface 42d of the first elastic member 90 is formed in a step section formed on an upper end side of the inner circumferential surface 42n.

A positioning member 42z extending upward is formed in the inward projecting part 42t. The positioning member 42z fits in a positioning groove 61u (see FIG. 12) formed on an outer circumferential surface of the shaft section 61.

Consequently, positioning in a circumferential direction of the shaft section 61 in the through-hole 42h is performed. Note that the rigid cylinder 42 may be made of resin.

The elastic cylinder 41 includes, in a position 41b at a lower end in contact with the exterior member 103g, a second elastic member 41q locked to the flange section 23f of the nut 23 when the attachment section 40 is attached to the cylinder member 30.

Note that the second elastic member 41q may be formed integrally with the elastic cylinder 41. A function of the second elastic member 41q is described below.

When the rigid cylinder 42 is made of resin, a material configuring the second elastic member 41q is desirably a material having self-adhesiveness to the rigid cylinder 42.

For example, when the rigid cylinder 42 is made of polycarbonate, the second elastic member 41q and the elastic cylinder 41 are desirably made of a polyester-based elastomer resin.

When the rigid cylinder 42 is made of polypropylene, the second elastic member 41q and the elastic cylinder 41 are desirably made of styrene-based thermoplastic elastomer resin.

Further, it has been known as a result of an experiment that, when the rigid cylinder 42 is made of polysulfone, the second elastic member 41q and the elastic cylinder 41 are desirably made of silicon.

Consequently, since an adhesive does not have to be used for formation of the elastic cylinder 41 on the rigid cylinder 42, it is possible to reduce molding cost and machining cost of the piston member 60.

Note that a material configuring the second elastic member 41q and the elastic cylinder 41 is not limited to the materials described above and may be any material as long as the material has self-adhesiveness to the rigid cylinder 42 and has elasticity.

In the compression spring 80, the one end 80a is in contact with the suction button 64 and the other end 80b is in contact with the inward projecting part 42t. That is, the compression spring 80 is suspended along the extending direction P between the suction button 64 and the rigid cylinder 42.

The compression spring 80 urges the piston member 60 in the upward direction P1 with respect to the rigid cylinder 42.

That is, in a state in which the suction button 64 is not operated by the operator, as shown in FIG. 7, the suction button 64 is located to project upward from the attachment section 40 by the compression spring 80.

In this case, as shown in FIG. 5 to FIG. 7, a gap S1 is formed between the suction button 64 and the attachment section 40.

Note that other components of the conduit control device 50 are the same as the components of the conventional conduit control device. Therefore, explanation of the components is omitted.

An operation for switching the communication state of the suction conduit 10 using the conduit control device 50 configured as described above is briefly explained below.

First, as shown in FIG. 7, the second elastic member 41q is locked to the flange section 23f of the nut 23. Consequently, in a state in which the piston unit 70 is attached to the cylinder member 30, the piston member 60 is pushed in the upward direction P1 by an urging force of the compression spring 80 in a natural state in which the suction button 64 is not depressed by the operator.

In the natural state shown in FIG. 7, the suction conduit 10a communicates with an outside of the operation section 103 via the second opening section 30v, the piston insert through-hole 30i, the opening 61v, the communication path 61i, the through-hole 61w, the through-hole 42h, and the gap S1.

That is, the suction pump 139 sucks atmospheric air outside the operation section 103 via the tube 138, the suction conduit 10a, the second opening section 30v, the piston insert through-hole 30i, the opening 61v, the communication path 61i, the through-hole 61w, the through-hole 42h, and the gap S1.

In this case, as shown in FIG. 7, since an outer circumferential surface 61g of the shaft section 61 closes the first opening section 30w of the cylinder member 30, the suction pump 139 does not suck the inside of the subject via the suction conduit 10b and the opening 10k.

Subsequently, as shown in FIG. 8, when the first elastic member 90 is depressed by the operator in a direction (hereinafter referred to as downward direction) P2 on an opposite side of the upward direction P1 in the extending direction P resisting the urging force of the compression spring 80 until the first elastic member 90 comes into contact with the contact surface 42d of the inner circumferential surface 42n of the rigid cylinder 42, a closed state of the first opening section 30w on the outer circumferential surface 61g of the shaft section 61 is released.

Therefore, the suction conduit 10a communicates with the second opening section 30v, the piston insert through-hole 30i, the opening 61v, the communication path 61i, the through-hole 61w, the first opening section 30w, the suction conduit 10b, and the opening 10k.

That is, the suction pump 139 sucks at least one of the solid and the fluid inside the subject via the tube 138, the suction conduit 10a, the second opening section 30v, the piston insert through-hole 30i, the opening 61v, the communication path 61i, the through-hole 61w, the first opening section 30w, the suction conduit 10b, and the opening 10k.

In this case, the first elastic member 90 is elastically deformed by being pressed against the contact surface 42d in the downward direction P2 to thereby seal the gap S1.

The second elastic member 41q is elastically deformed by being pressed against the nut 23 and the exterior member 103g in the downward direction P2 to thereby seal a gap S2 between the elastic cylinder 41 and the exterior member 103g and the gap S2 between the attachment section 40 and the cylinder member 30.

Therefore, since the gaps S1 and S2 are sealed, a suction amount of the suction pump 139 does not decrease. The suction pump 139 can surely suck at least one of the solid and the fluid from the inside of the subject.

Note that other operations of the conduit control device 50 are the same as the operations of the conventional conduit control device. Therefore, explanation of the operations is omitted.

As described above, in the present embodiment, when the suction button 64 is depressed in the downward direction P2 by the operator in order to suck at least one of the solid and the fluid inside the subject, the first elastic member 90 provided in the suction button 64 is elastically deformed by being pressed against the contact surface 42d provided on the inner circumferential surface 42n of the rigid cylinder 42 to thereby seal the gap S1 between the piston member 60 and the attachment section 40.

It is further explained that, when the suction button 64 is depressed in the downward direction P2 by the operator, the second elastic member 41q is elastically deformed by being pressed against the nut 23 and the exterior member 103g in the downward direction P2 to thereby seal the gap S2 between the elastic cylinder 41 and the exterior member 103g and the gap S2 between the attachment section 40 and the cylinder member 30.

Consequently, even if the elastic cylinder 41 including the second elastic member 41q is configured from a member having elasticity in order to seal the gap S2, the first elastic member 90 can surely seal the gap S1 by coming into contact with the contact surface 42d of the rigid cylinder 42 rather than the elastic cylinder 41 to be elastically deformed.

Consequently, even if the shaft section 61 is made of resin and a gap is formed between the outer circumferential surface 61g of the shaft section 61 and an inner circumferential surface 30n of the cylinder member 30, it is possible to surely secure air-tightness in the conduit control device 50 at the time when the suction button 64 is depressed. Therefore, it is possible to prevent the suction amount from decreasing.

According to the above explanation, it is possible to provide the conduit control device 50 including a configuration in which it is possible to sufficiently secure the suction amount of the suction conduit 10 in the communication state.

Figure 9:
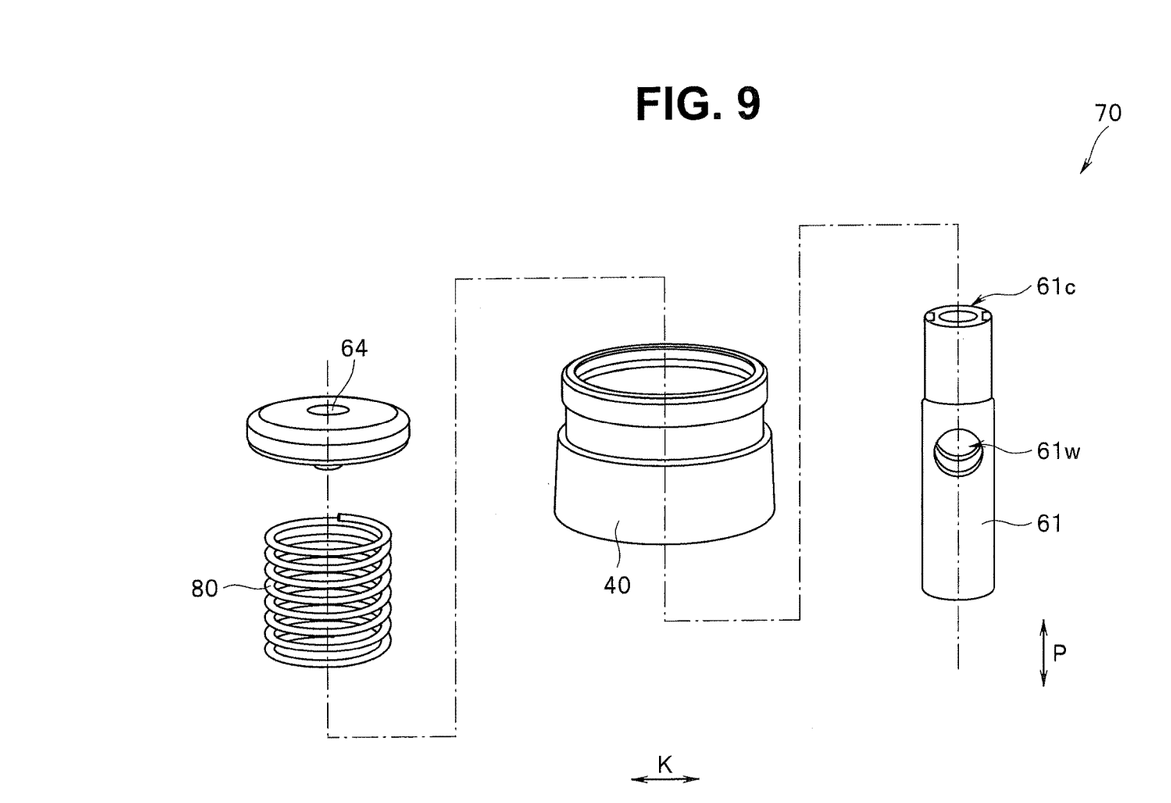
FIG. 9 is an exploded perspective view of the piston unit shown in FIG. 4.

Note that another modification is described below with reference to FIG. 9. FIG. 9 is an exploded perspective view of the piston unit shown in FIG. 4.

In the present embodiment described above, it is explained that the suction button 64 is fixed to the top of the shaft section 61 by the screwing and bonding.

Independently of this, as shown in FIG. 9, after the compression spring 80 and the shaft section 61 are assembled to the attachment section 40, the suction button 64 may be fixed to a top surface 61c of the shaft section 61 by ultrasonic welding.

With such a configuration, an adhesive does not have to be used for the fixing of the suction button 64. Moreover, the number of components can be reduced more than in a structure in which the suction button 64 is fixed to the top surface 61c of the shaft section 61 via a not-shown plurality of components. Therefore, it is possible to reduce manufacturing cost.

Figure 10:
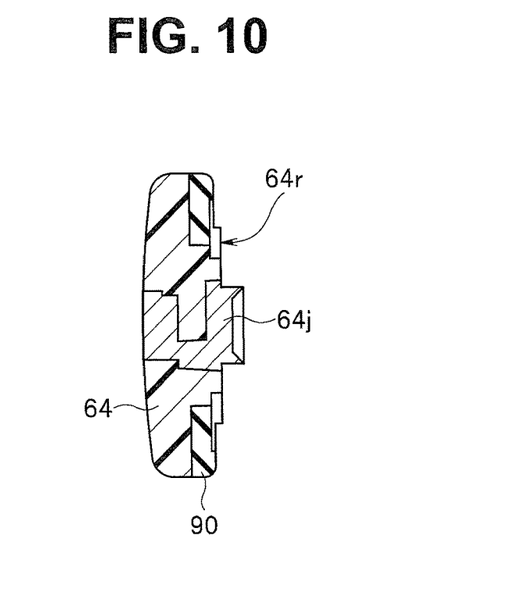
FIG. 10 is a sectional view of a suction button shown in FIG. 9 in a configuration of a modification.
Figure 11:
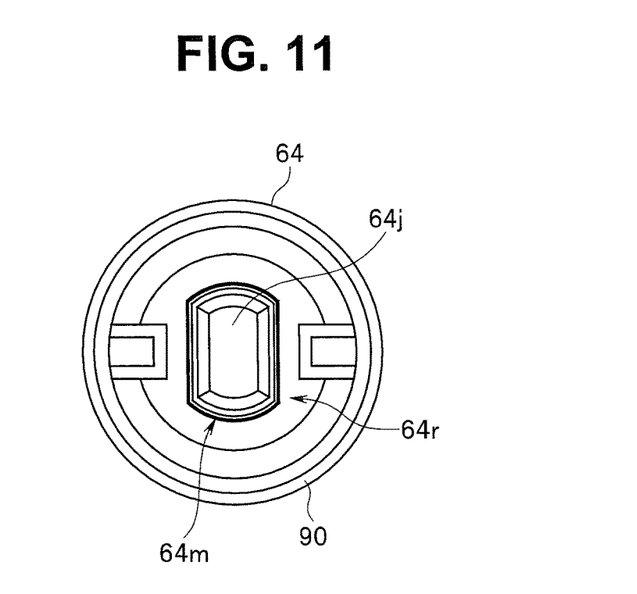
FIG. 11 is a bottom view of the suction button shown in FIG. 10 viewed from a bottom surface side.
Figure 12:
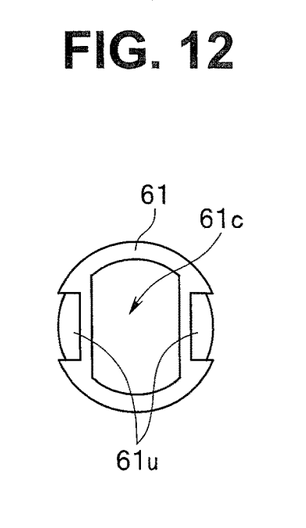
FIG. 12 is a top view of a top surface of a shaft section shown in FIG. 9 in a configuration of a modification.

Another modification is described below with reference to FIG. 10 to FIG. 12. FIG. 10 is a sectional view of the suction button shown in FIG. 9 in a configuration of the modification. FIG. 11 is a bottom view of the suction button shown in FIG. 10 viewed from a bottom surface side. FIG. 12 is a top view of a top surface of the shaft section shown in FIG. 9 in the configuration of the modification.

As shown in FIG. 12, for positioning in the circumferential direction of the shaft section 61 with respect to the attachment section 40, the positioning groove 61u, in which the positioning member 42z fits, is formed on the top surface 61c of the shaft section 61. Therefore, a welding area of the suction button 64 on the top surface 61c is small.

Therefore, as shown in FIG. 10 and FIG. 11, a plane shape of a welding section 64j on a rear surface 64r of the suction button 64 may be formed in an oval shape.

Consequently, since a welding region 64m of the welding section 64j to the top surface 61c is also formed in an oval shape, the welding area is sufficiently secured. Therefore, it is possible to sufficiently secure welding strength of the suction button 64 to the shaft section 61.

Figure 13:
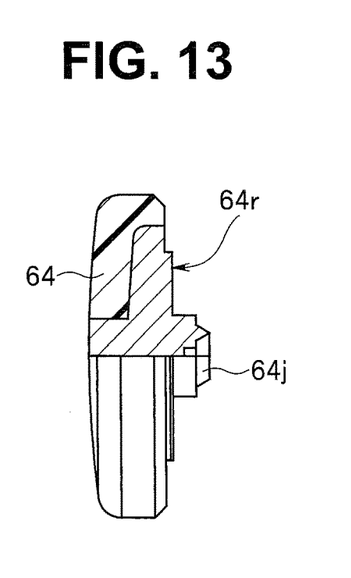
FIG. 13 is a partial sectional view of the suction button shown in FIG. 9 in a configuration of a modification different from the configuration of the modification shown in FIG. 10.
Figure 14:
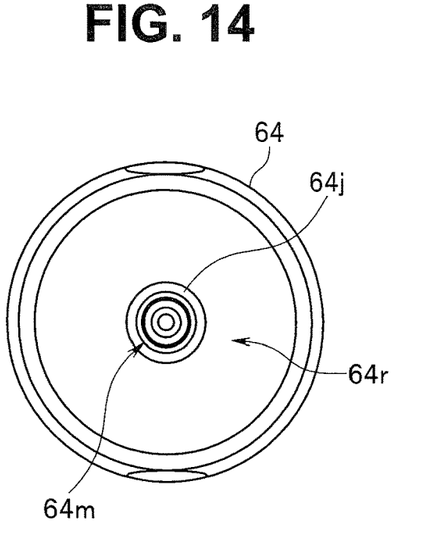
FIG. 14 is a bottom view of the suction button shown in FIG. 13 viewed from the bottom surface side.
Figure 15:
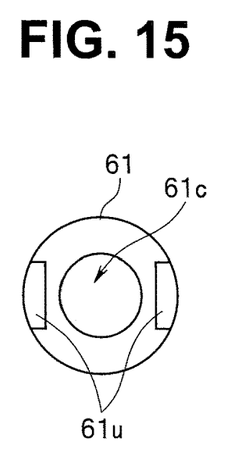
FIG. 15 is a top view of a top surface of the shaft section shown in FIG. 9 in a configuration of a modification different from the configuration of the modification shown in FIG. 12.

Another modification is described below with reference to FIG. 13 to FIG. 15. FIG. 13 is a partial sectional view of the suction button shown in FIG. 9 in a configuration of a modification different from the configuration of the modification shown in FIG. 10. FIG. 14 is a bottom view of the suction button shown in FIG. 13 viewed from the bottom surface side. FIG. 15 is a top view of a top surface of the shaft section shown in FIG. 9 in a configuration of a modification different from the configuration of the modification shown in FIG. 12.

As shown in FIG. 13 and FIG. 14, the plane shape of the welding section 64j on the rear surface 64r of the suction button 64 may be formed in a circular shape.

Consequently, the welding area is small compared with the oval shape shown in FIG. 11. However, since the welding region 64m is also formed in a circular shape, a welding direction of the suction button 64 in the circumferential direction to the top surface 61c can be neglected. Therefore, the suction button 64 is easily assembled. Moreover, it is possible to reduce an assembly time.

Note that, in the embodiment described above, it is explained that the conduit control device 50 switches the communication state of the suction conduit 10.

Independently of this, it goes without saying that the present invention is also applicable to a configuration in which communication states of other conduits are switched.

What is claimed is:

1. A conduit control device for use with an operation section of an endoscope, the conduit control device switching a communication state of a conduit provided inside the endoscope, the conduit control device comprising:
   a cylinder member;
   a piston member, a shaft section of which is provided to be slidable into the cylinder member, the piston member including a button section at a top of the shaft section;
   an attachment section including a rigid cylinder being configured to be detachably attachable to a vicinity of an opening of the cylinder member in an exterior of the operation section, the attachment section including a through-hole through which the shaft section is inserted and an elastic cylinder integrally formed on an outer circumferential surface of the rigid cylinder;
   a compression spring suspended between the button section and the rigid cylinder, the compression spring urging the piston member with respect to the rigid cylinder in a direction in which the button section projects from the opening; and
   a first elastic member, the first elastic member being disposed further in the projection direction from where the compression spring contacts the button section, the first elastic member further being brought into contact with a contact surface, which is provided on an inner circumferential surface of the rigid cylinder, and elastically deformed to thereby seal a gap between the attachment section and the piston member in a state in which the piston member is depressed via the button section,
   wherein the elastic cylinder includes a second elastic member, the second elastic member being configured to be in contact with the exterior of the operation section, the second elastic member further being configured to be brought into contact with the exterior and elastically deformed to thereby seal a gap between the attachment section and the exterior in a state in which the piston member is depressed via the button section.

2. The conduit control device according to claim 1, wherein the first elastic member is disposed on a radial direction outer side of the button section with respect to the position at which the one end of the compression spring comes into contact in the button section.

3. The conduit control device according to claim 1, wherein another end of the compression spring is in contact with an inward projecting part provided on the inner circumferential surface of the rigid cylinder.

4. The conduit control device according to claim 1, wherein the second elastic member is formed integrally with the elastic cylinder.

5. The conduit control device according to claim 1, wherein the contact surface is formed in a step section of the inner circumferential surface of the rigid cylinder.

6. The conduit control device according to claim 1, wherein the piston member is made of resin.

7. The conduit control device according to claim 1, wherein
- an upstream side and a downstream side of the conduit are connected to the cylinder member, and
- the upstream side and the downstream side communicate with each other in a state in which the piston member is depressed.

8. The conduit control device according to claim 1, wherein the conduit is a suction conduit for sucking at least one of a solid and a fluid from a distal end of an insertion section of the endoscope.

* * * * *